US010475319B2

(12) United States Patent
Janscha et al.

(10) Patent No.: US 10,475,319 B2
(45) Date of Patent: **\*Nov. 12, 2019**

(54) PORTABLE GENERATOR INCLUDING CARBON MONOXIDE DETECTOR

(71) Applicant: Briggs & Stratton Corporation, Wauwatosa, WI (US)

(72) Inventors: Ryan D. Janscha, Brookfield, WI (US); David W. Procknow, Elm Grove, WI (US); Brandon Nigh, Elm Grove, WI (US); Mark David Willer, Brookfield, WI (US)

(73) Assignee: Briggs & Stratton Corporation, Wauwatosa, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/395,171

(22) Filed: Apr. 25, 2019

(65) Prior Publication Data

US 2019/0251817 A1    Aug. 15, 2019

Related U.S. Application Data

(63) Continuation of application No. 15/886,627, filed on Feb. 1, 2018, now Pat. No. 10,319,207.

(60) Provisional application No. 62/455,373, filed on Feb. 6, 2017, provisional application No. 62/453,823, filed on Feb. 2, 2017.

(51) Int. Cl.
| | | |
|---|---|---|
| *G08B 17/11* | (2006.01) | |
| *G08B 17/117* | (2006.01) | |
| *G08B 3/00* | (2006.01) | |
| *G08B 5/22* | (2006.01) | |
| *H02H 7/06* | (2006.01) | |
| *G01N 33/00* | (2006.01) | |
| *H02K 7/00* | (2006.01) | |
| *H02K 7/18* | (2006.01) | |

(52) U.S. Cl.
CPC ......... *G08B 17/117* (2013.01); *G01N 33/004* (2013.01); *G08B 3/00* (2013.01); *G08B 5/224* (2013.01); *H02H 7/06* (2013.01); *H02K 7/00* (2013.01); *H02K 7/1815* (2013.01)

(58) Field of Classification Search
CPC .... G08B 17/117; G08B 5/224; G01N 33/004; H02H 7/06
USPC ......................................................... 340/632
See application file for complete search history.

(56) References Cited

U.S. PATENT DOCUMENTS

| | | |
|---|---|---|
| 3,703,162 A | 11/1972 | Aono |
| 5,793,296 A | 8/1998 | Lewkowicz |

(Continued)

FOREIGN PATENT DOCUMENTS

WO    WO-2018/035434 A1    2/2018

*Primary Examiner* — Omar Casillashernandez
(74) *Attorney, Agent, or Firm* — Foley & Lardner LLP

(57) ABSTRACT

A generator includes an engine, an air-fuel mixing device coupled to the engine, where the air-fuel mixing device is structured to receive air from an air intake and combine the air with fuel to create an air/fuel mixture, an exhaust outlet positioned on a first side of the generator and coupled to the engine, wherein the exhaust outlet is structured to emit exhaust gases from the engine, and a carbon monoxide (CO) sensor positioned on a second side of the generator opposite the exhaust outlet, where the CO sensor is structured to detect CO concentration near the generator.

13 Claims, 14 Drawing Sheets

(56) References Cited

U.S. PATENT DOCUMENTS

| | | | |
|---|---|---|---|
| 6,222,349 B1* | 4/2001 | LeRow | H02J 7/1453 |
| | | | 322/33 |
| 6,983,726 B1* | 1/2006 | Luo | B60H 1/00314 |
| | | | 123/179.2 |
| 8,286,603 B2 | 10/2012 | Sid | |
| 8,375,913 B2* | 2/2013 | Kwiecinski | F02N 11/0807 |
| | | | 123/179.2 |
| 8,413,642 B2 | 4/2013 | Johnson et al. | |
| 8,534,258 B2* | 9/2013 | Cristoforo | F02D 41/042 |
| | | | 123/198 D |
| 8,939,134 B2 | 1/2015 | Sato et al. | |
| 9,058,739 B2 | 6/2015 | Sid | |
| 9,175,601 B2 | 11/2015 | Markoski | |
| 9,293,914 B2 | 3/2016 | Mauk et al. | |
| 2003/0091430 A1* | 5/2003 | Mulera | F01D 21/04 |
| | | | 415/14 |
| 2007/0085692 A1* | 4/2007 | Grant | G08B 21/14 |
| | | | 340/632 |
| 2008/0015794 A1* | 1/2008 | Eiler | F24F 3/16 |
| | | | 702/33 |
| 2009/0240377 A1* | 9/2009 | Batzler | G05B 23/0216 |
| | | | 700/287 |
| 2013/0110376 A1* | 5/2013 | Surnilla | F02D 41/042 |
| | | | 701/103 |
| 2013/0168969 A1* | 7/2013 | Markoski | F01N 3/103 |
| | | | 290/1 A |
| 2016/0258387 A1 | 9/2016 | Markoski | |

\* cited by examiner

PORTABLE GENERATOR INCLUDING CARBON MONOXIDE DETECTOR

CROSS-REFERENCE TO RELATED PATENT APPLICATION

This is a continuation of U.S. application Ser. No. 15/886,627, filed Feb. 1, 2018, which claims the benefit of U.S. Provisional Patent Application No. 62/455,373, filed Feb. 6, 2017 and U.S. Provisional Patent Application No. 62/453,823, filed Feb. 2, 2017, all of which are incorporated herein by reference in their entireties.

BACKGROUND

The present invention generally relates to internal combustion engines and generators powered by such engines. More specifically, the present invention relates to a carbon monoxide (CO) detection system for a generator.

SUMMARY

One embodiment of the invention relates to a generator. The generator includes an engine, an air-fuel mixing device coupled to the engine, where the air-fuel mixing device is structured to receive air from an air intake and combine the air with fuel to create an air/fuel mixture, an exhaust outlet positioned on a first side of the generator and coupled to the engine, where the exhaust outlet is structured to emit exhaust gases from the engine, and a carbon monoxide (CO) sensor positioned on a second side of the generator opposite the exhaust outlet, where the CO sensor is structured to detect CO concentration near the generator. In some embodiments, the generator includes a CO sensor controller structured to control operation of the CO sensor. The CO sensor controller includes a shutdown circuit structured to determine an environment of the generator and determine a predetermined threshold CO concentration for the determined environment. In some embodiments, the shutdown circuit determines the environment of the generator by calculating a variance of a first derivative of output values from the CO sensor. In some embodiments, the shutdown circuit determines the environment of the generator by calculating a standard deviation of output values from the CO sensor. In some embodiments, the shutdown circuit determines the environment of the generator by calculating a peak-to-peak range of output values from the CO sensor. In some embodiments, the shutdown circuit determines the environment of the generator by calculating curve kurtosis of output values from the CO sensor. In some embodiments, the shutdown circuit receives generator run time information and determines a predetermined threshold based on the detected environment and the generator run time.

Another embodiment of the invention relates to a generator. The generator includes an engine, an air-fuel mixing device coupled to the engine, where the air-fuel mixing device is structured to receive air from an air intake and combine the air with fuel to create an air/fuel mixture, an exhaust outlet structured to emit exhaust gases from the engine, a CO sensor structured to detect CO concentration near the generator, and a CO sensor controller. The CO sensor controller is coupled to the CO sensor and structured to control operation of the CO sensor. The CO sensor controller includes a shutdown circuit structured to determine an environment of the generator and an alert circuit structured to receive an alert indication from the shutdown circuit and alert a user of the generator to the detected CO concentration. the shutdown circuit determines the environment of the generator by calculating a maximum variance of output values from the CO sensor. In some embodiments, the shutdown circuit determines the environment of the generator by calculating a slope variance of output values from the CO sensor. In some embodiments, the shutdown circuit determines the environment of the generator by calculating a variance of a first derivative of output values from the CO sensor. In some embodiments, the shutdown circuit determines the environment of the generator by calculating a standard deviation of output values from the CO sensor. In some embodiments, the shutdown circuit determines the environment of the generator by calculating a peak-to-peak range of output values from the CO sensor. In some embodiments, the shutdown circuit determines the environment of the generator by calculating curve kurtosis of output values from the CO sensor. In some embodiments, the alert circuit is further structured to transmit an alert notification to a mobile device upon receiving the indication from the shutdown circuit. In some embodiments, the shutdown circuit receives generator run time information and determines a predetermined threshold based on the detected environment and the generator run time.

Another embodiment of the invention relates to method of shutting down a generator including an internal combustion engine. The method includes determining, by a CO sensor controller, an environment of the generator, the environment including at least one of an enclosed environment and an open environment, determining, by the CO sensor controller, a first predetermined threshold for the enclosed environment and a second predetermined threshold for the open environment, and completing, by the CO sensor controller, a shutdown procedure upon determining the generator is in the enclosed environment and the first predetermined threshold is exceeded.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
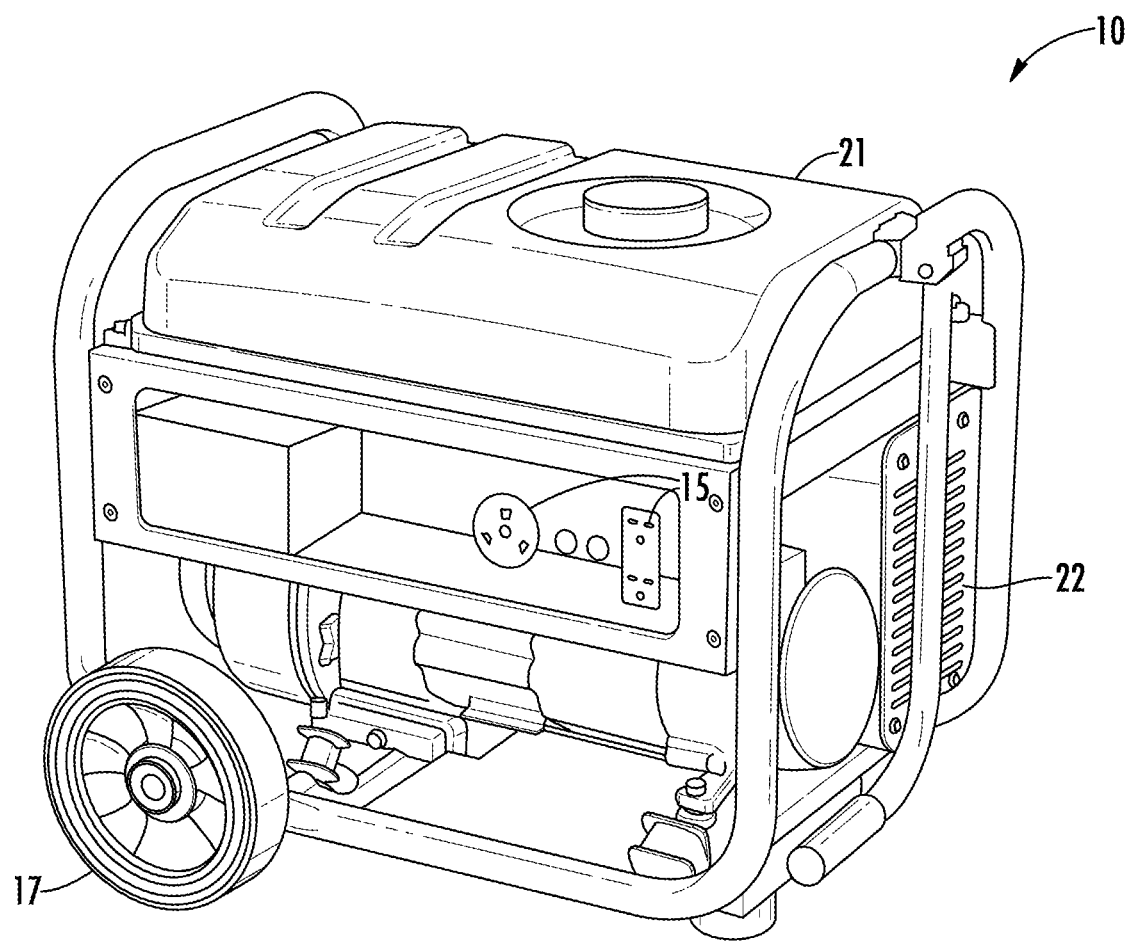
FIG. 1 is a perspective view of a generator according to an exemplary embodiment of the invention.
Figure 2:
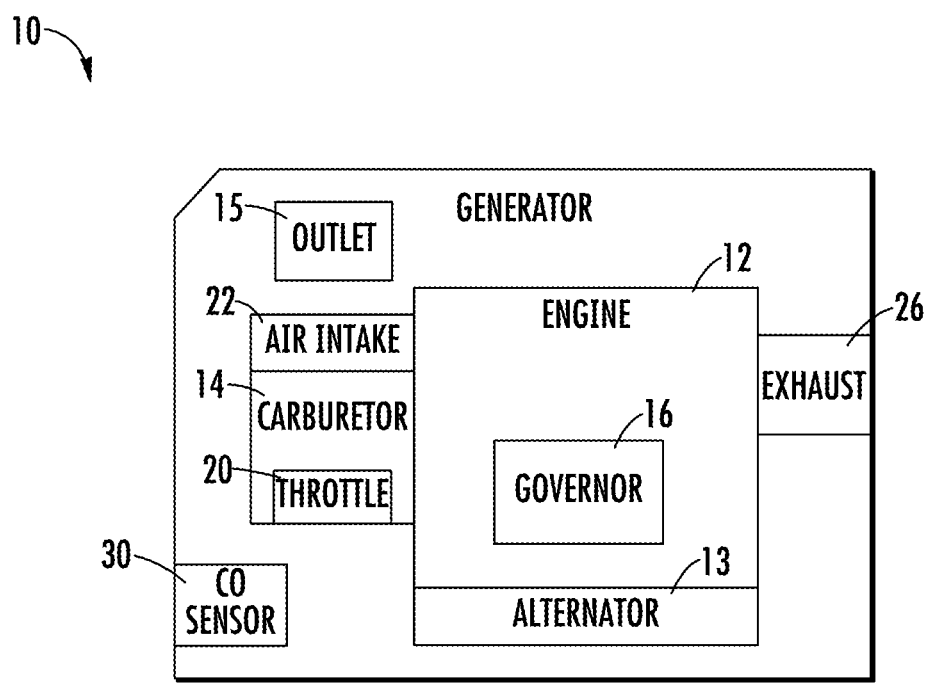
FIG. 2 is a schematic diagram of a generator according to an exemplary embodiment of the invention.

Referring to FIGS. 1-2, a generator is shown according to an exemplary embodiment. The generator 10 includes an engine 12, including a carburetor 14 or other air-fuel mixing device (e.g., electronic fuel injection, direct fuel injection, etc.), governor 16, throttle 20, air intake 22, exhaust outlet 26, and an alternator 13 driven by the engine 12. The alternator 13 produces electrical power from input mechanical power from the engine 12. The generator 10 additionally includes one or more outlets 15 for supply of the generated electrical power to an electrical device of a user's choosing. The generator 10 can also include one or more wheels 17 for portability. In some embodiments, a fuel tank 21 is positioned at the top of the generator 10 with the exhaust outlet 26 positioned below the fuel tank 21.

Air flows into the engine 12 from the air intake 22 and through the carburetor 14. As air passes through the carburetor 14, the air mixes with fuel entering the carburetor 14 from the fuel tank 21 and creates an air/fuel mixture that then enters the engine 12. The throttle 20 controls the flow of the air/fuel mixture that exits the carburetor 14. The governor 16 controls the position of the throttle 20 based on a detected load on the engine 12. The air/fuel mixture leaving the carburetor 14 is combusted in one or more cylinders of the engine 12 and exhaust gas from combustion leaves the engine 12 through the exhaust outlet 26. The exhaust gas is primarily made up of nitrogen, water vapor, and carbon dioxide, but a portion of the exhaust gas may be carbon monoxide (CO) from incomplete combustion. Operation of a generator (or any other equipment powered by an engine) in a non-ventilated space (e.g., volume), such as a garage, home, or storage unit, can result in accumulation of CO within the space over time.

As shown in FIG. 2, the generator 10 includes a CO sensor 30 configured to detect the concentration of CO (e.g., parts per million (ppm)). Additionally, the CO sensor 30 may be used with other types of outdoor power equipment. Outdoor power equipment includes lawn mowers, riding tractors, snow throwers, pressure washers, portable generators, tillers, log splitters, zero-turn radius mowers, walk-behind mowers, riding mowers, industrial vehicles such as forklifts, utility vehicles, etc. Outdoor power equipment may, for example, use an internal combustion engine to drive an implement, such as a rotary blade of a lawn mower, a pump of a pressure washer, the auger a snow thrower, the alternator of a generator, and/or a drivetrain of the outdoor power equipment. Portable jobsite equipment includes portable light towers, mobile industrial heaters, and portable light stands.

Figure 3:
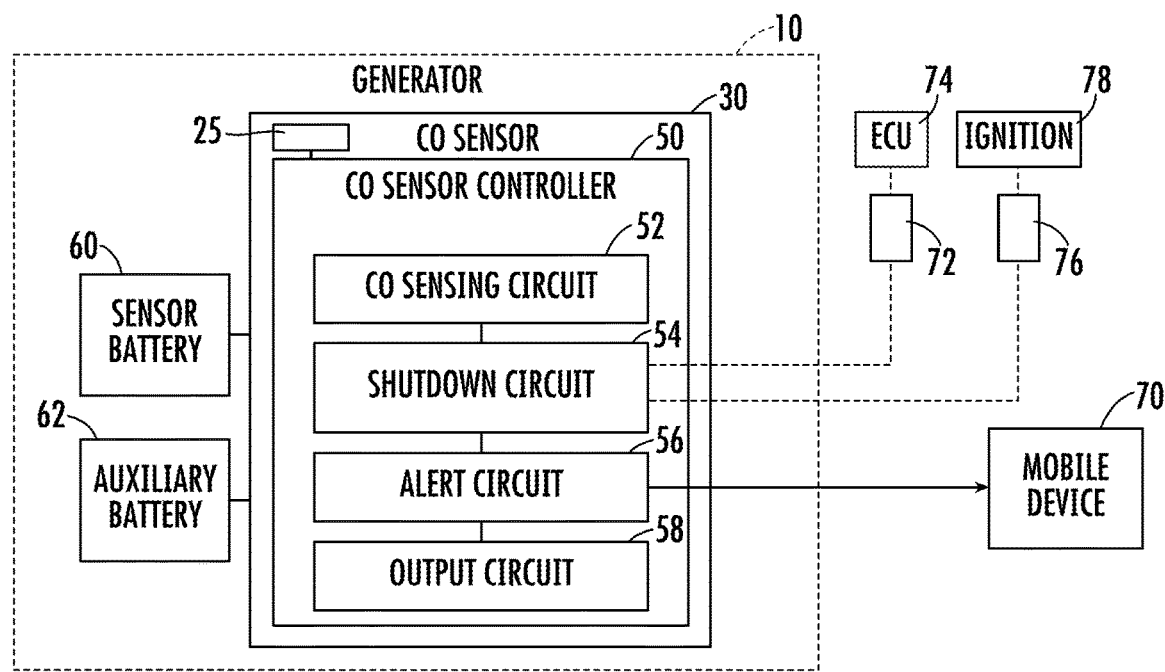
FIG. 3 is a schematic diagram of a carbon monoxide detection sensor of the generator of FIGS. 1 and 2, according to an exemplary embodiment of the invention.

Referring now to FIG. 3, a schematic diagram of the CO sensor 30 is illustrated, according to an exemplary embodiment. In some embodiments, the CO sensor 30 includes a metal oxide gas sensor unit 25. The metal oxide gas sensor unit 25 detects CO concentration via a gas sensitive film that is composed of tin or tungsten oxides. The sensitive film reacts with CO to determine CO concentration at the sensor unit 25. In other embodiments, the CO sensor 30 can include an electrochemical sensor. The electrochemical sensor measures the concentration of CO at the sensor by oxidizing or reducing the gases at an electrode and measuring the resulting current. The sensor unit 25 is positioned above all other components of the CO sensor 30. In other embodiments, the sensor unit 25 is otherwise positioned.

The CO sensor 30 alerts a user to an elevated concentration of CO exceeding the predetermined threshold and controls the shutdown of the generator 10 in these instances. Additionally, as discussed further herein, the CO sensor 30 includes control circuitry to determine when detections of an elevated CO concentration may be fleeting (e.g., short spikes in signal readings). Fleeting elevated CO concentration detections may be due to movement of the surrounding air rather than unwanted accumulation of CO over a period of time. Movement of the surrounding air can, under certain conditions, introduce the CO sensor 30 to CO laden exhaust from the generator 10. This can cause transient spikes in the CO level as read by the sensor 30.

The CO sensor 30 includes or is coupled to a CO sensor controller 50 configured to control the operations of the CO sensor 30, including but not limited to, timing of generator shutdown and alerts, transmitting an alert to a user, triggering a visual alarm (e.g., indicator light), triggering an audible alarm (e.g., alarm bell), shutting down the generator, etc. To perform the functions described herein, the CO sensor controller 50 can include a processing circuit, which includes a processor and a memory. The processor may be implemented as a general-purpose processor, an application specific integrated circuit (ASIC), one or more field programmable gate arrays (FPGAs), a digital signal processor (DSP), a group of processing components that may be distributed over various geographic locations or housed in a single location, or other suitable electronic processing components. The one or more memory devices (e.g., RAM, NVRAM, ROM, Flash Memory, hard disk storage) may store data and/or computer code for facilitating the various processes described herein. Moreover, the one or more memory devices may be or include tangible, non-transient volatile memory or non-volatile memory. Accordingly, the one or more memory devices may include database components, object code components, script components, or any other type of information structure for supporting the various activities and information structures described herein.

The CO sensor controller 50 includes a CO sensing circuit 52, a shutdown circuit 54, and an alert circuit 56, with all such circuits communicably coupled to each other. The CO sensing circuit 52 is configured to receive sensor output values from the CO sensor 30 relating to the detected CO concentration and communicate the CO concentration to the shutdown circuit 54 and alert circuit 56. Accordingly, the CO sensing circuit 52 is communicably and operatively coupled to the shutdown circuit 54 and alert circuit 56 to provide the CO concentration values. The CO concentration values may be provided in terms of output voltage values which are proportional to the CO ppm values. The CO sensor controller 50 may additionally include a database configured to store sensed CO values over time and corresponding response actions (e.g., generator shutdown, alert transmission, alert signal, self-diagnostics, etc.).

The shutdown circuit 54 is configured to receive the detected CO values from the CO sensing circuit 52, determine whether the generator 10 is in an enclosed space or an open space, and determine whether to shut down the generator 10 and/or provide a triggered alarm response to the detection. Upon receiving the detected CO concentration values (e.g., correlating output voltage values) from the CO sensor 30, the shutdown circuit 54 first determines if the generator 10 is likely in an enclosed space or an open space. Depending on the location of the generator 10 relative to open or enclosed spaces, the shutdown circuit 54 will treat sensed CO concentration data differently. To determine the environment of the generator 10, the shutdown circuit 54 may use a variety of methods. In many of the methods, the shutdown circuit 54 uses time lapse information to perform calculations. Accordingly, a timing circuit may be included with the generator 10 to determine the amount of time the generator 10 has been running. To determine run time, electrical output from the generator, spark plug data, and/or electric starter data may be used to determine the start of the generator operation, the duration of generator operation, the number of engine starting or stopping events within a certain period of time, etc. Additionally, calculations may be reset due to a sensed movement of the generator 10. Movement of the generator 10 can be sensed via a piezoelectric sensor positioned on the generator 10 configured to measure acceleration data.

In one embodiment, the shutdown circuit 54 calculates and monitors the variance in the sensed CO concentration values. To continually monitor the variance, the shutdown circuit 54 compares the current calculated variance to the previously calculated variances for a single generator run. In this regard, the shutdown circuit 54 may temporarily store the readings relating to one or more data samples in a database incorporated with the CO sensor controller 50. To calculate variance, the shutdown circuit 54 uses the equation below for each sample reading time frame.

$$\sigma^2 = \frac{\sum_{i=1}^{N}(ppm_i - \overline{ppm})^2}{N}$$

In the above equation, sigma squared is the variance of the output signal read from the CO sensor 30, "ppm" is the sample reading, "$\overline{ppm}$" is the average ppm over the sample window, "i" is the current sample number, and "N" is the sample window. Sample readings are taken at 10 hertz and the sample window is approximately 15 seconds. In other embodiments, sample readings are taken more or less frequently. Applicant believes that sample windows of less than 5 seconds are too small to perform the contemplated control schemes.

Figure 9:
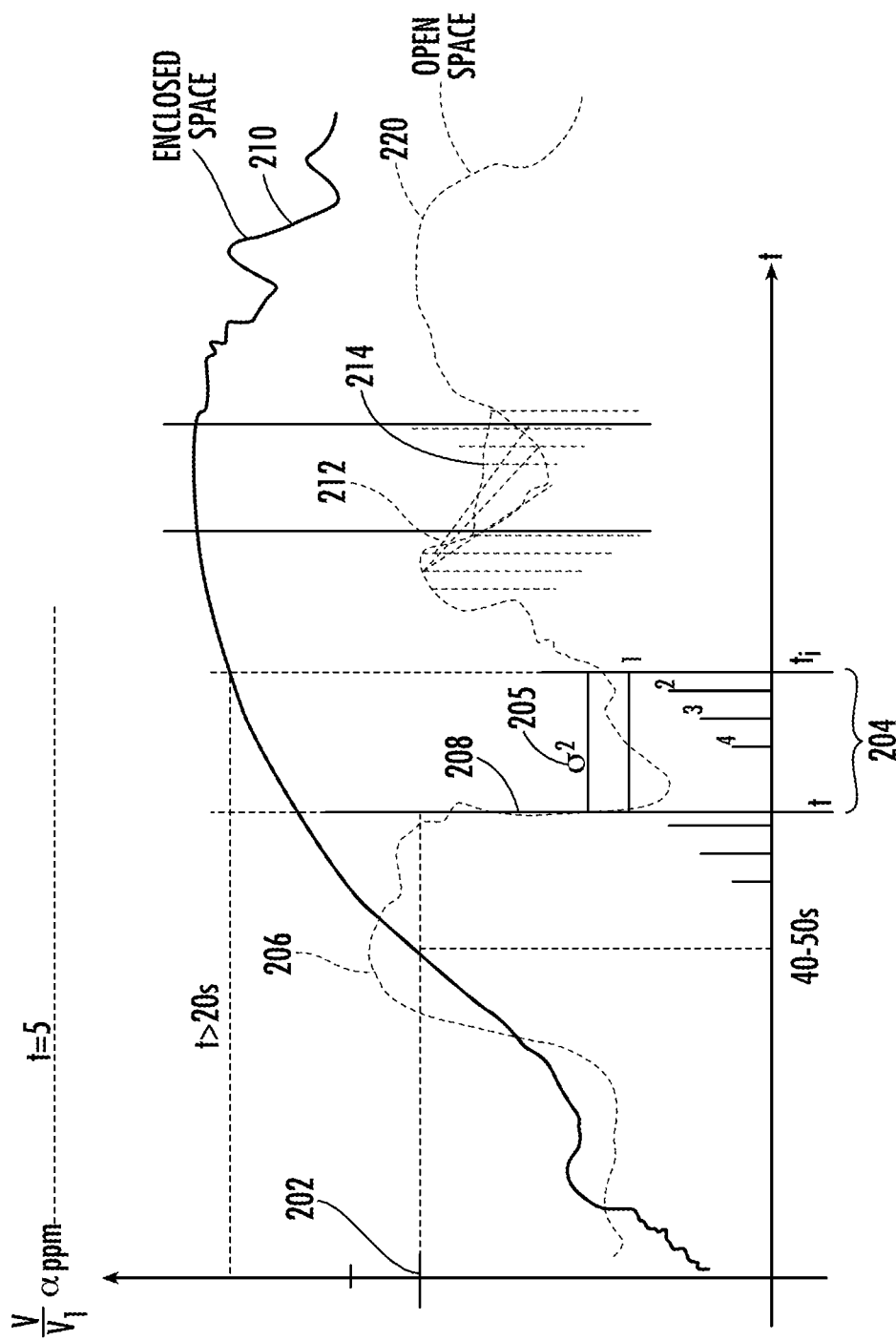
FIG. 9 is a graph of the generator operating time plotted against carbon monoxide detection levels, according to an exemplary embodiment of the invention.

By determining variance using an equation such as the one above, the shutdown circuit 54 determines whether the generator 10 is in an enclosed space (e.g., garage) and potentially experiencing settled accumulations of CO or in an open space (e.g., outside) and experiencing brief spikes in readings of the CO concentrations (e.g., due to air movement surrounding the generator 10). The variance of the sensed values indicates how much the sensed values vary from their average and thus, whether the sensed readings are choppy or smooth when graphed over time (see FIG. 9 showing sensor output value versus time). When sensed readings increase and decrease rapidly over time with a relatively high variance, that may be an indication the generator 10 is in an open space. When sensed readings change smoothly over time (e.g., steadily increase) with relatively low variance, that may be an indication the generator 10 is in an enclosed space.

If the variance is calculated to be relatively high, the shutdown circuit 54 determines that the generator 10 is positioned in an open environment and may use a different sensed CO threshold to shut down the generator 10 than if the variance is calculated to be relatively low. As an example, if the variance is calculated to be relatively low, the shutdown circuit 54 determines that the generator 10 is likely positioned in an enclosed space and shuts down the generator 10 at a lower CO ppm reading or within a smaller time frame than if determined to be in an open space.

In some embodiments, the shutdown circuit 54 may additionally or alternatively use the calculated maximum variance over a number of sample readings to determine whether the generator 10 is in an enclosed space or an open space. The shutdown circuit 54 continues to calculate variance as described above, while monitoring the maximum value of variance calculated over time. The maximum variance calculated for an enclosed space (e.g., garage) will be typically lower than the maximum variance calculated for an open space (e.g., outside). Maximum variance curves vary less than the variance curves described above and thus, may be useful in that the distinction between a graphed maximum variance value for an enclosed space and an open space is relatively clear. As such, a maximum variance boundary can be predetermined such that above the boundary, the generator 10 is determined to be in an open space and below the boundary, the generator 10 is determined to be in an enclosed space. Applicant believes that a rolling window for 30 seconds provides optimal detection of maximum variance values and that a window of greater than 45 seconds may risk slowing shutdown reaction times in enclosed spaces.

In some embodiments, the shutdown circuit 54 may alternatively or additionally use slope variance calculations to determine whether a generator 10 is in an enclosed or open space. The shutdown circuit 54 uses the derivative of the graphed line for the signal readings over time to determine the slope of the graph at the specific point in time. The change in the slope calculations over time can be used to determine whether the generator 10 is in an enclosed space or an open space. For example, if the slope changes from positive to negative, the shutdown circuit 54 may determine that the generator 10 is in an open space. Frequent changes between positive and negative slope may also indicate the generator 10 is in an open space. Additionally, if there are no slope changes from positive to negative, the shutdown circuit 54 may determine that the generator 10 is in an enclosed space. Likewise, a variance of the sampled slopes may also be used to discern open space and enclosed space running of the generator.

The shutdown circuit 54 may additionally set an absolute maximum CO concentration threshold such that upon reaching the threshold, the generator 10 is shut down. Accordingly, at any point in time regardless of the environment in which the generator 10 is positioned, when an absolute CO threshold concentration (e.g., >1000 ppm of CO) is detected, the generator 10 is shut down.

In some embodiments, the shutdown circuit 54 also uses the overall lapsed time since the generator 10 was started to determine a sensed value threshold for shut down. For example, for a time period of less than two minutes, the shutdown circuit 54 uses one set of threshold values to determine when to shut down the generator 10 and for one or more subsequent operating periods (e.g., between two and five minutes, between five and ten minutes, greater than fifteen minutes, etc.), the shutdown circuit 54 uses a different set of threshold values. For the initial operating period, the shutdown circuit 54 has lower threshold values for triggering a shutdown or alarm than the subsequent operating periods. Any false alarm or shutdown triggers may be less inconvenient to a user while the user is still near the generator 10 (e.g., less time has passed), than if the user has already left the area. For time periods of greater than thirty minutes, the threshold may be even less sensitive to being triggered. In other embodiments, other time periods can be used. Once the generator 10 moves into subsequent operating periods, the controller can be more confident that the generator is not operating in an enclosed space and can reduce the sensitivity and reduce the occurrence of unwanted shutdowns. Because CO typically accumulates quickly in an enclosed space, it is beneficial to be relatively sensitive to elevated CO concentrations in that environment and shutdown the generator.

The combination of parameters including time-since-startup (t), max variance ($\sigma^2$max) and CO level (ppm) can be combined to best guard against CO accumulations during enclosed space running, while minimizing nuisance shutdowns. During initial operation (e.g., less than 5 minutes), maximum variance is monitored to a higher threshold (e.g., maximum variance is less than 0.005). As an example, a generator shutdown is triggered for CO concentrations greater than a threshold of greater than 300 ppm of CO only if the maximum variance is less than 0.005. Conversely, if run-time is greater than 5 minutes, a generator shutdown is not triggered for detected CO concentrations until maximum variance is less than 0.003. Furthermore, the CO concentration threshold for triggering a shutdown during this time period is raised to greater than 400 ppm of CO. To provide a redundant layer of protection, generator shutdown is triggered if a detected CO concentration of greater than 400 ppm has persisted for longer than 15 seconds, regardless of variance.

In some embodiments, the shutdown circuit 54 may additionally or alternatively use other calculation methods to determine whether the generator 10 is in an enclosed or an open space. The shutdown circuit 54 may use any method to detect and amplify the characteristics (e.g., choppy versus smooth) of the detected CO concentration versus time curve. For example, standard deviation, variance of the first derivative, peak-to-peak range, curve kurtosis, or other custom functions may be used to determine the environment of the generator 10.

The shutdown circuit 54 can use various other sensors to determine whether the generator 10 is in an enclosed or an open space. The sensors can include, but are not limited to, an ambient lighting sensor, an acoustic sensor, radar sensor, wind speed sensor, Global Positioning System (GPS) mapping, and so on.

Once the shutdown circuit 54 has determined whether the generator 10 is in an enclosed or open space, the shutdown circuit 54 triggers shutdown and/or alerts upon detection of a predetermined threshold for that environment. In this regard, the shutdown circuit 54 is coupled to an engine shutdown circuit of the engine 12 to complete a shutdown procedure. The shutdown circuit 54 is also communicably and operatively coupled to the alert circuit 56 to communicate an indication that a threshold level has been reached for an alert to be triggered. The response of the shutdown circuit 54 to a CO concentration threshold may be dependent on the determined environment. For example, the shutdown circuit 54 determines that the generator 10 is outside due to a high variance calculation and a spike of 100 ppm of CO is detected. In this case, the shutdown circuit 54 may take no action because of the consideration that the spike of CO concentration may be due to temporary blow back of exhaust gases on the CO sensor 30. As another example, the shutdown circuit 54 determines that the generator 10 is in an enclosed space. With the same detection of 100 ppm of CO, the generator 10 may communicate with the alert circuit 56 to alert a user by sounding an alarm, triggering an indicator light, and/or transmitting an alert to a mobile device 70 of the user. The alarm may be paired with a shutdown of the generator 10 and/or a warning of potentially elevated CO concentration without shutting down the generator 10.

Still referring to FIG. 3, in some embodiments, the shutdown circuit 54 is communicably and operatively coupled to a wiring harness 72 coupled to an electronic control unit (ECU) 74. The ECU 74 is configured to control the operations of the generator 10. Thus, the ECU 74 is capable of completing a shutdown procedure for the generator 10. The wiring harness 72 is configured to interface with the ECU 74 and communicate potential shutdown signals received from the shutdown circuit 54. In this situation, a bipolar junction transistor (BJT) opto-isolator is used to relay the communication to the ECU 74. In other embodiments, the shutdown circuit 54 is communicably and operatively coupled to a wiring harness 76 coupled to the ignition 78 of the generator 10. The shutdown procedure can include grounding the ignition for a period of time (e.g., 10 seconds) until the engine 12 is turned off. In this situation, an opto-isolated triode for alternating current (TRIAC) is used to ground the ignition for a period of time to accomplish a shutdown. Depending on whether the engine has an ECU 74 or not, the appropriate output from the shutdown circuit 54 can be used. In some embodiments, both outputs are included in the CO sensor 30 so that the same sensor may be used with different types of engines, either as original equipment or as an after-market addition to the generator 10.

The alert circuit 56 is configured to communicate with the shutdown circuit 154 to receive an indication that the generator 10 has been shut down due to sensed CO accumulation or an indication of an elevated CO concentration. The alert circuit 56 is additionally configured to trigger an alarm system on the generator including, but not limited to, an indicator light and an audible alarm. In this configuration, if the user is signaled that the shutdown is due to CO emissions build-up in a non-ventilated space, the user is less likely to try to start the generator back up. The alert circuit 56 may trigger varying levels of alarms corresponding to the sensed concentration of CO, with alarm severity increasing with the increasing CO concentration (e.g., warning light, warning audible alarm and then shut down, etc.). In some embodiments, the alert system is powered by a separate power supply than the sensing element (e.g., sensor unit 25) to prolong the shutdown capability of the system.

Two indicator lights are included with the generator 10 including a CO light indicator and a self-diagnostic light indicator. The CO light indicator is configured to indicate that the sensed concentration of CO is above a predetermined threshold. The self-diagnostic light indicator is configured to indicate that the generator 10 is self-testing and/or that the generator 10 has diagnosed an error or fault condition. The self-diagnostic light indicator may change colors based on the indication presented (e.g., green for self-testing, red for fault condition, etc.). Light pipes are included with the generator 10 to allow the indicator lights to be seen regardless of the position of the CO sensor 30. The light pipes are positioned to extend from the indication located on the board to a position easily visible to a user. The light pipes allow for optimal board positioning, while still allowing visibility of the indicator lights. In addition, the light pipes and remote board positioning allows for simplification and ease of use across various types of generators. In addition to indicator lights, the generator 10 can also include audio alerts, scroll text, etc.

In some embodiments, the alert circuit 56 is configured to switch over a mechanical switch to an elevated CO concentration indication position when a shutdown of the generator 10 occurs due to the detection of accumulated CO. Accordingly, the user will be notified of the CO detection by the physical location of the switch even though the generator 10 has been shut down and no electrical (e.g., sound or light) indication may be present. In the case of a shutdown switch, before starting the generator 10 back up after a shutdown, the user must first physically move the switch from the elevated CO concentration indication position back to an operating position. In some embodiments, the generator 10 may additionally include tamper resistant sensors. Accordingly, a user cannot easily disconnect or circumvent the sensors described herein. For example, power and communication wires to and from the CO sensor 30 may be combined in a single wire harness.

Figure 8:
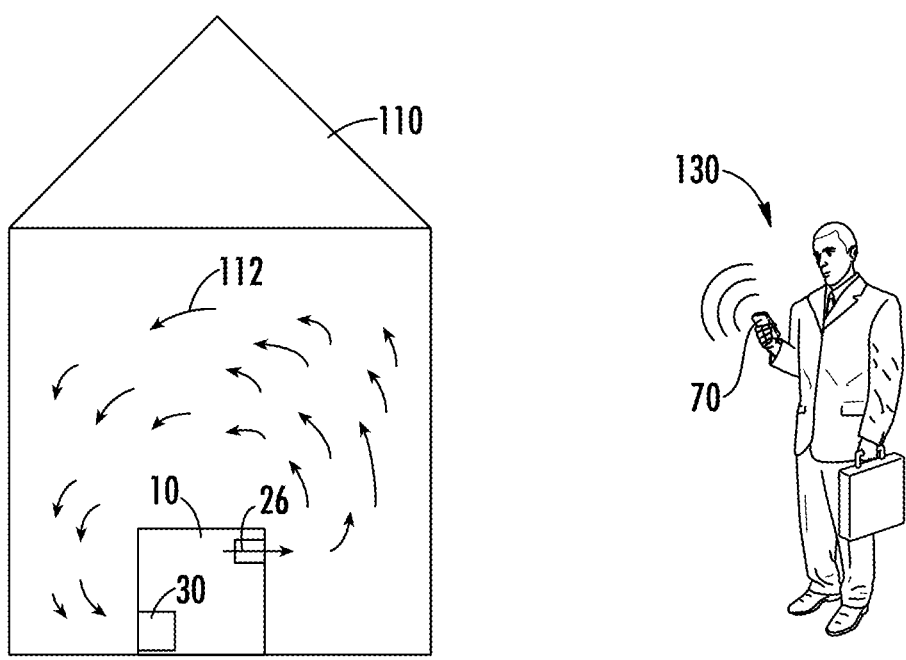
FIG. 8 is a diagram of the generator operating in an inside environment, according to an exemplary embodiment of the invention.

In some embodiments, the alert circuit 56 is additionally configured to communicate with a mobile device 70 to alert a user that the generator 10 has been shut down due to sensed CO accumulation. Accordingly, the user may be alerted on the mobile device 70 (as shown in FIG. 8) while the user is away from the generator 10 and can proceed with caution if re-entering the enclosed space.

The output circuit 58 is configured to communicate with the various circuits (e.g., CO sensing circuit 52, shutdown circuit 54, alert circuit 56) of the CO sensor controller 50 to gather the operations taken by the CO sensor controller 50 and any output data generated by the CO sensor controller 50. The output circuit 58 is further configured to provide the gathered operations to a communication output such that a user may connect a device to the output to determine the operations and outputs of the CO sensor controller 50. The communication output includes a serial communication interface allowing for connection to the controller 50 for reception and transmission of data (e.g., operations of the controller 50). As an example, a device connected to the communication output can receive and decode a generated light blink pattern to determine a fault code associated with the light pattern.

One or more batteries are included to power the CO sensor unit 25 and the other components of the sensor 30. In some embodiments, the batteries are lithium-ion coin cell batteries. In other embodiments, the batteries may use different battery chemistries and/or structural configurations. A sensor battery 60 is coupled to the CO sensor unit 25 to provide power to the CO sensor unit 25. The sensor battery 60 continues to provide power to the CO sensor unit 25 even when the generator 10 is shut down. This way, the CO sensor unit 25 is still actively monitoring CO concentration (e.g., via pulse detection) when the generator 10 is not running. The continuous operation of the CO sensor unit 25 allows the unit 25 to continue to monitor the CO concentration in the vicinity of the generator 10 and prevents the unit 25 from resetting the baseline CO reading to zero ppm upon turning off power from the generator to the sensor unit 25. Without continuous supply of power to the sensor unit 25 from the sensor battery 60, the sensor unit 25 may normalize the CO reading to zero ppm upon receiving power (even in areas with CO present), and accordingly, the CO reading may be skewed if power is not continuously supplied to the CO sensor unit 25. In addition, because the sensor battery 60 powers the CO sensor 30 separately, the CO sensor 30 can be used on various non-power generating equipment, such as lawn mowers, power washers, etc.

An auxiliary battery 62 can also be coupled to the CO sensor 30 to provide power to the auxiliary systems included with the CO sensor 30, such as an alert light, an audible alarm, sensor self-diagnostics, etc. Like the sensor battery 60, the auxiliary battery 62 may also provide continuous power to the auxiliary systems of the sensor 30. Accordingly, an alert may still be transmitted, sounded, lit, etc. when the generator 10 is off. In some embodiments, the sensor battery 60 and the auxiliary battery 62 include high-capacity capacitors (e.g., supercapacitor) to prevent power loss when the generator 10 is off.

Figure 4:
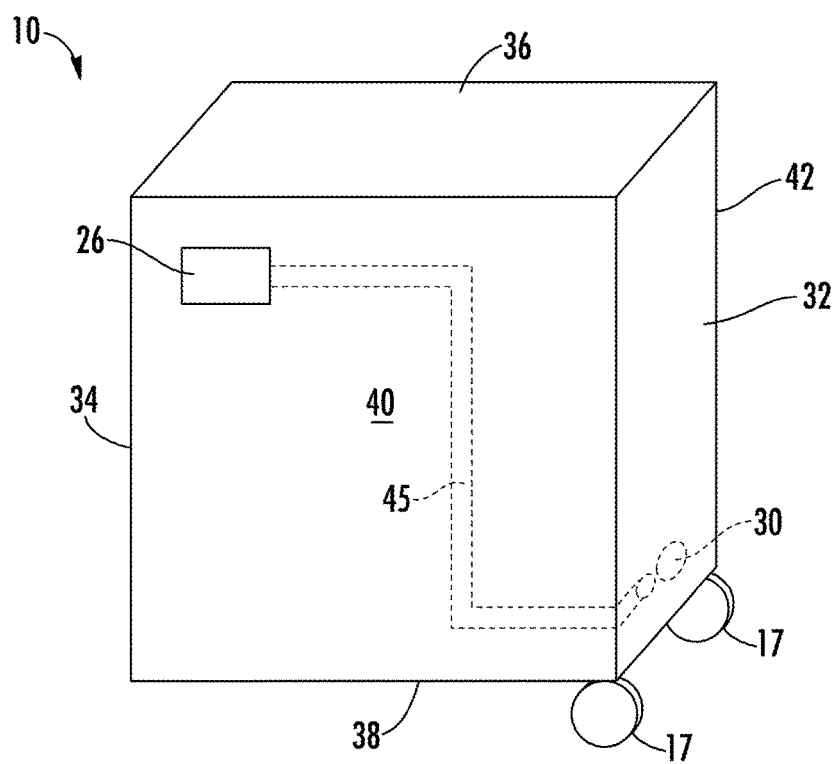
FIG. 4 is a perspective view of the generator of FIG. 1, according to an exemplary embodiment of the invention.
Figure 5:
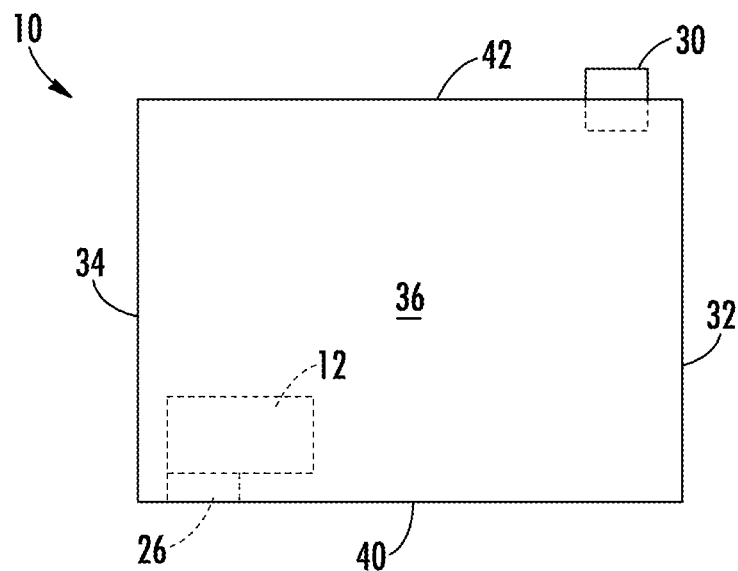
FIG. 5 is a top view of the generator of FIG. 1, according to an exemplary embodiment of the invention.

Referring to FIGS. 4-5, the generator 10 includes a front 32, rear 34, top 36, bottom 38, left side 40, and right side 42. As shown in FIG. 4, the CO sensor 30 is positioned on the right side 42 near the front 32, while the exhaust outlet 26 is positioned on the left side 40 near the rear 34. In other embodiments, the CO sensor 30 may be positioned on another side of the generator 10 (e.g., front 32). While not limited to the exact positioning illustrated in FIGS. 4-5, the positioning of the CO sensor 30 is preferably selected such that exhaust gases exiting the exhaust outlet 26 are not blown back directly onto the CO sensor 30 in an environment with wind and/or air movement toward the exhaust outlet 26. Accordingly, when viewing the generator 10 from above as shown in FIG. 5, the CO sensor 30 is positioned on an opposite side of the generator 10 from the exhaust outlet 26 (e.g., diagonally opposite, directly opposite). In some embodiments, when viewed from above, the CO sensor 30 is positioned on an opposite side of the generator 10 from the engine 12 with the engine 12 located between the sensor 30 and the exhaust outlet 26. Positioning the sensor 30 as described helps to broaden the difference in variance seen in enclosed space versus open space running.

Additionally, the CO sensor 30 is positioned at an elevation lower than the exhaust outlet 26. Due to the relatively higher temperature of exhaust gases compared to atmospheric temperatures, the exhaust gases will rise upon exit from the exhaust outlet 26. Accordingly, positioning the CO sensor 30 at an elevation lower than the exhaust outlet 26 helps to prevent the continuous passing of exhaust gases over the CO sensor 30 during normal operation, while still allowing detection of elevated concentrations of CO due to accumulation over a period of time.

As shown in FIG. 4, the generator 10 includes a redirect channel or conduit 45 assembled as part of the generator 10 to route exhaust gases exiting the exhaust outlet 26 to the CO sensor 30. The redirect channel 45 directs the exhaust gases (or a portion of the exhaust gases) to the CO sensor 30 upon exiting the exhaust outlet 26 (or prior to exiting the exhaust outlet 26). As such, the redirect channel 45 allows for testing of the CO sensor 30 installation and operation prior to shipment of the generator 10 and/or CO sensor 30 to an end customer by sending exhaust gases to the sensor 30 to verify proper response from the sensor 30 in the presence of exhaust gases. After testing and ensuring the CO sensor 30 works properly, the redirect channel 45 may be plugged or removed to ensure that no false shutdowns or indications occur due to the redirect channel 45 when the generator 10 is in normal use. In other embodiments, the generator 10 does not include a redirect channel.

Figure 6:
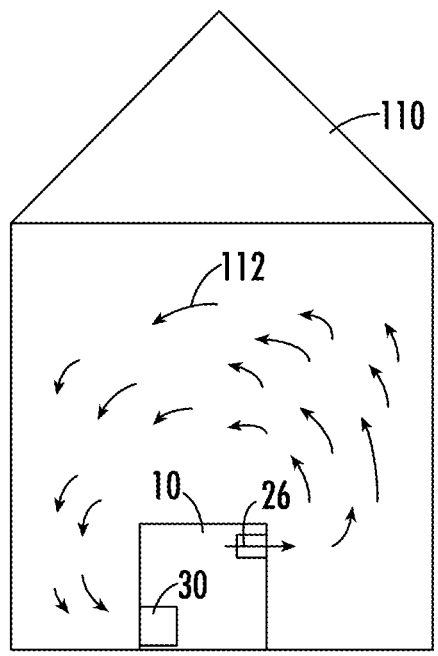
FIG. 6 is a diagram of the generator operating in an inside environment, according to an exemplary embodiment of the invention.

Referring now to FIG. 6, a generator operating within an enclosed environment is shown. The generator 10 is positioned within an enclosure 110 such that the exhaust gases 112 exiting the exhaust outlet 26 accumulate within the enclosure 110 over a period of time. As shown, the exhaust gases fill the space within the enclosure 110 and are eventually directed toward the CO sensor 30, where the concentration of CO is detected. In the enclosed environment, the CO concentration will rise more steadily and quicker than in the open environment shown in FIG. 7.

Figure 7:
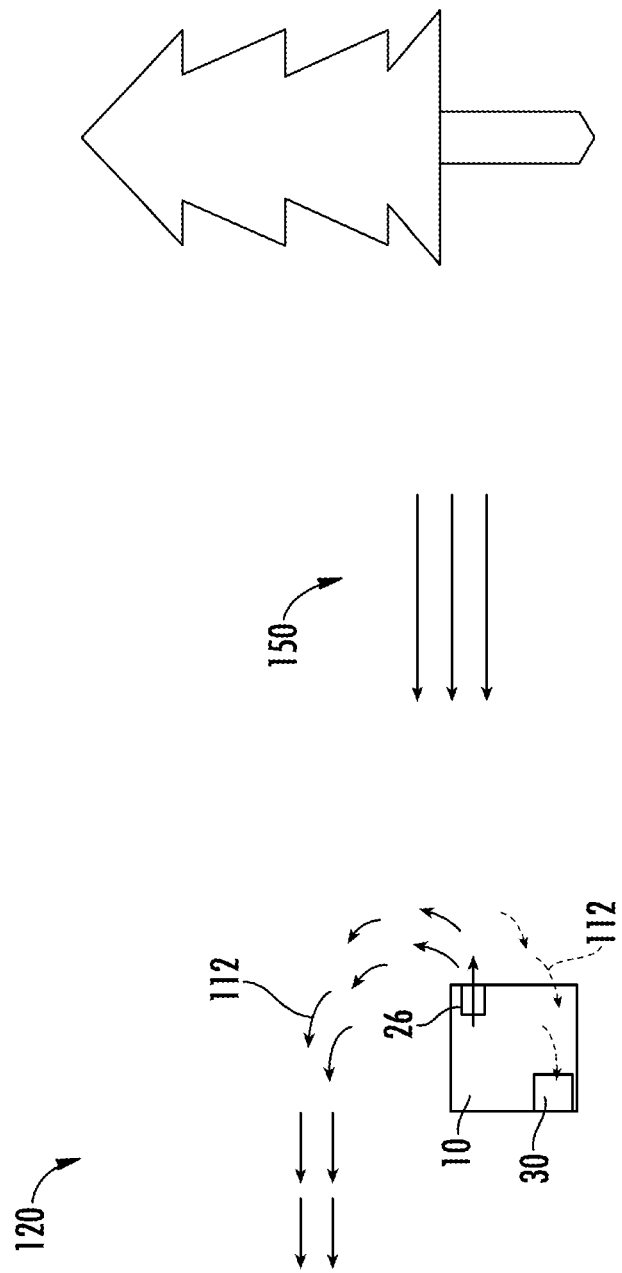
FIG. 7 is a diagram of the generator operating in an outside environment, according to an exemplary embodiment of the invention.

Referring now to FIG. 7, a generator operating in an open environment is shown. The generator 10 is positioned in an open space 120. In the open space 120 the generator 10 is exposed to air movement 150 that may occur due to wind. As the air movement 150 passes over the generator 10, the exhaust gases exiting from the exhaust outlet 26 are redirected in the direction of the air movement 150 and pass back over the generator 10 resulting in blow back of exhaust gases washing over the CO sensor 30. As described above with regard to FIGS. 4 and 5, the CO sensor 30 is positioned on the opposite side of the generator 10 and below the exhaust outlet 26 such that any blow back of exhaust gases resulting from air movement 150 are not directed toward the CO sensor 30. Accordingly, the CO sensor 30 can determine more accurately whether the generator 10 is in the enclosed environment shown in FIG. 6 or in the open environment shown in FIG. 7. The placement of the CO sensor 30 relative to the exhaust outlet 26 is important to accurately determine that the generator 10 is in an open space. If not positioned such that steady exhaust gas blow back on the sensor 30 is prevented, false low variation readings may be determined and the shutdown of the generator 10 may be triggered prematurely.

Referring now to FIG. 8, the generator operating in an enclosed environment is shown. In this instance, the user 130 is positioned away from the generator 10 and is carrying a mobile device 70. When the CO sensor 30 detects CO concentrations above a certain predetermined threshold as described above, the alert circuit 56 transmits a notification to the mobile device 70 of the user 130 to alert the user to the accumulated CO. Notifying the user 130 remotely can prevent the user 130 from walking into an area with concentrated CO.

As shown in FIG. 9, an example graph showing a CO sensor voltage output signal that is proportional to CO ppm versus time is illustrated. The graphed line 210 showing the enclosed space sensed values is overlaid with the graphed line 220 showing the open space sensed values. As shown, the enclosed space curve 210 smoothly increases, while the open space curve 220 increases and decrease rapidly with time. As described above, data within the sample window 204 is used to calculate the variance 205 between time t and $t_i$. In some embodiments, the slope 212 and slope variance 214 are additionally or alternatively calculated to determine whether the generator 10 is in an enclosed or open space. The CO concentration threshold 202 is used in part to determine the time at which to shut down the generator and/or provide an alert due to elevated CO concentration. As shown, the open space curve 220 extends above the threshold 202 at point 206 and quickly returns back below the threshold 202 at point 208, illustrating the high variance of the open space curve 202, while the enclosed space curve 210 steadily increases past the threshold 202.

Figure 10:
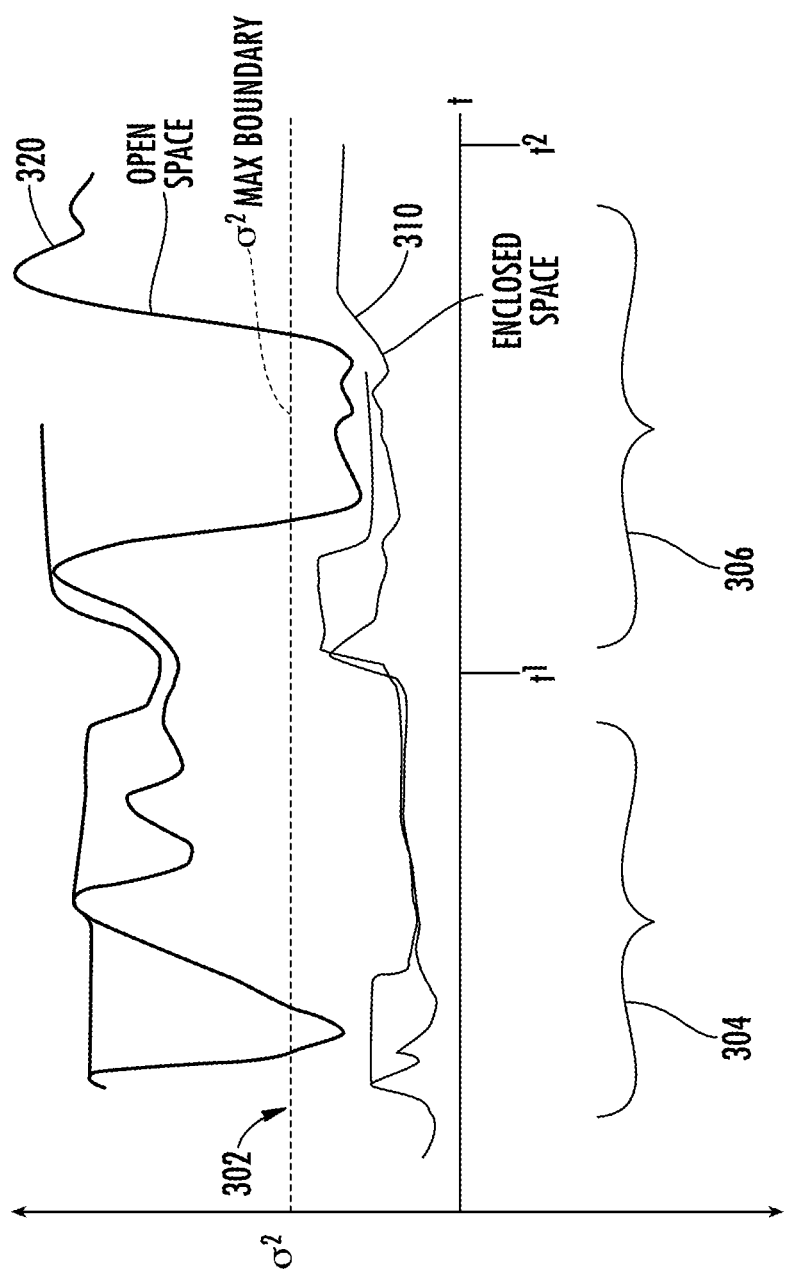
FIG. 10 is a graph of the generator operating time plotted against the variance of carbon monoxide detection levels, according to an exemplary embodiment of the invention.

As shown in FIG. 10, an example graph showing variances of enclosed space sensor data and open space sensor data versus time is illustrated. The enclosed space variance curve 310 and the open space variance curve 320 are overlaid versus time. The maximum value of the variance can be determined over the period of operation of the generator 10 and can be used to set a maximum variance boundary 302 (e.g., threshold) between an indication that the generator 10 is operating in an enclosed space (e.g., low maximum variance) and that the generator 10 is operating in an open space (e.g., high maximum variance). As such, the maximum variance boundary will be higher than the enclosed space maximum variance line and lower than the open space maximum variance line. If the maximum variance data being calculated for a particular generator is above the maximum variance boundary 302, the shutdown circuit 54 will determine that the generator is in an open space and if the maximum variance data calculated is below the maximum variance boundary, the shutdown circuit 54 will determine that the generator is in an enclosed space. An initial operating period 304 is also illustrated, where the shutdown circuit 54 may treat data in a more sensitive manner for triggering a shutdown or alarm than in subsequent operating periods (e.g., period 306).

Figure 11:
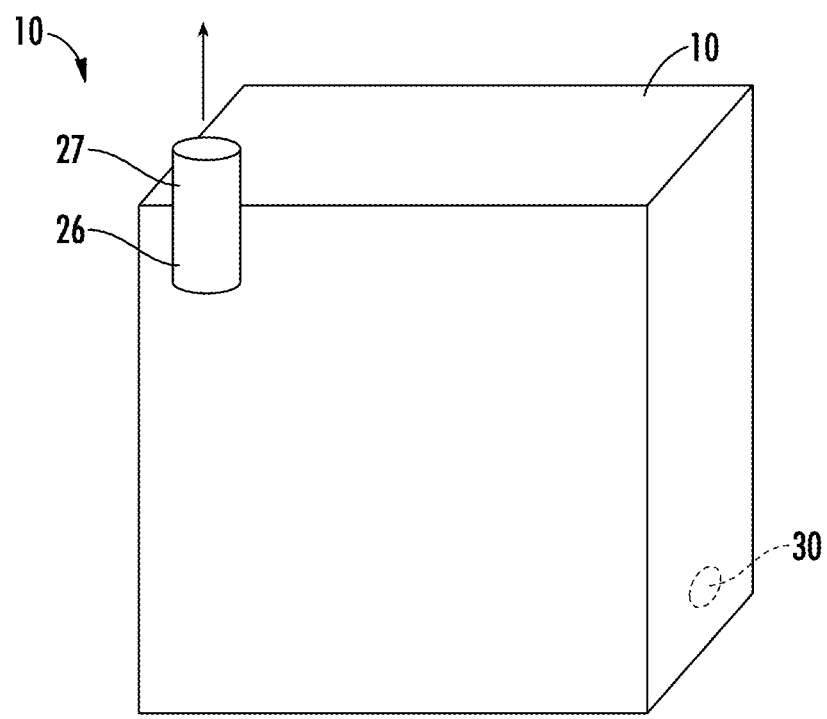
FIG. 11 is a perspective view of the generator of FIG. 1, according to an exemplary embodiment of the invention.

Referring now to FIG. 11, in some embodiments, the generator 10 includes an outlet duct 27 attached to the exhaust outlet 26 to direct exhaust gases up and away from the generator 10 and the CO sensor 30. As such, any air movement past the generator 10 (e.g., wind in an open space), will likely not blow the exhaust gases back onto the CO sensor 30 and instead, will direct the exhaust gases away from the generator 10 to prevent any premature generator shutdown or alert of elevated CO concentration readings.

Referring now to FIGS. 12-16, various graphs are shown relating to a number of tests conducted by the Applicant on a portable generator equipped with a CO sensor as described herein. The various graphs illustrate example data for the sensor output for a generator operating in an enclosed space, the sensor output for a generator operating in an open space, the measured ppm of CO in the enclosed space, the variance of the sensor output for the enclosed space, the variance of the sensor output for the open space, the maximum variance of the sensor output for the enclosed space, and the maximum variance of the sensor output for the open space, with all data measured over time.

Figure 12:
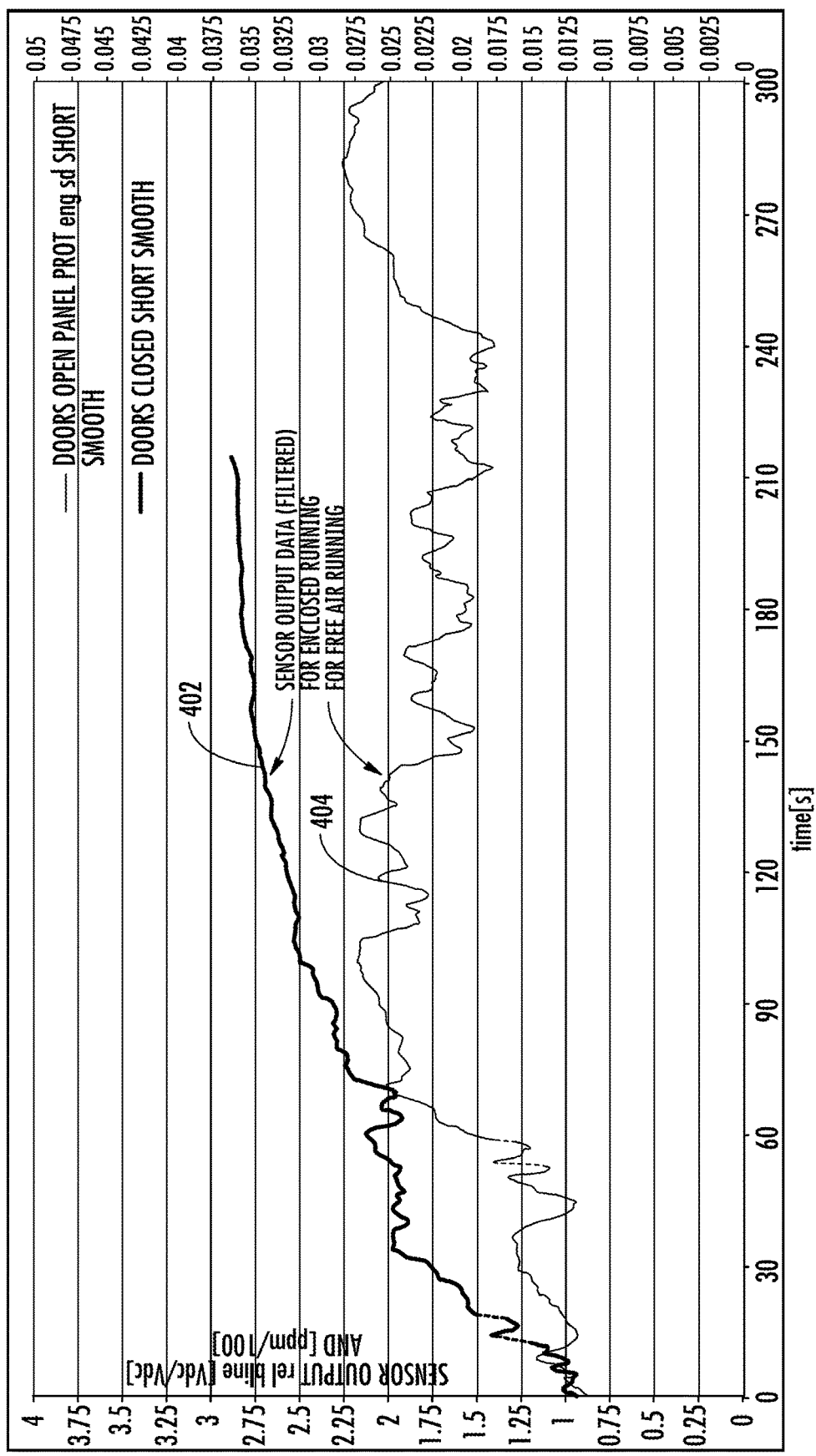
FIG. 12 is a graph of the generator operating time plotted against CO sensor output data.

Referring to FIG. 12, a graph plotting sensor output data for both enclosed and open environments against time is shown. As illustrated, the enclosed environment sensor output data 402 steadily increases over time as CO accumulates in the enclosed environment. The open environment sensor output data 404 shows a relatively unstable, highly variable CO sensor reading over time. As opposed to the enclosed environment sensor output data 402, the open environment sensor output data 404 does not increase over time and instead fluctuates around a mean value for the duration of the test.

Figure 13:
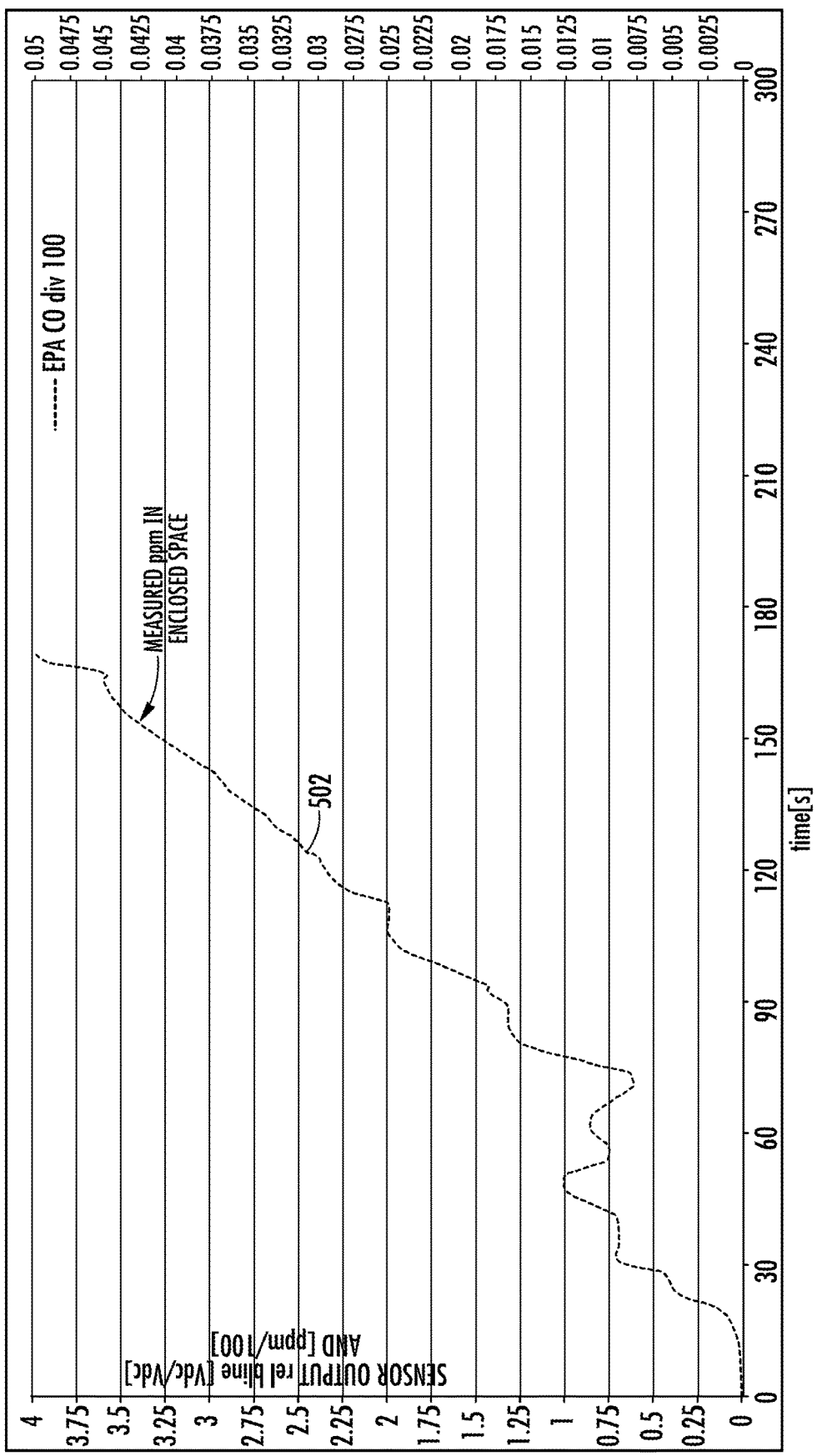
FIG. 13 is a graph of the generator operating time plotted against measured parts per million (ppm) of CO in an enclosed environment.

Referring to FIG. 13, a graph plotting measured ppm of CO in an enclosed space against time is shown. As illustrated by the graph, the measured ppm of CO 502 increases rapidly over time in an enclosed space as CO accumulates. For example, in a matter of approximately 120 seconds, the measured ppm of CO is approximately 300 ppm, and in approximately 150 seconds, the measured ppm of CO exceeds 375 ppm.

Figure 14:
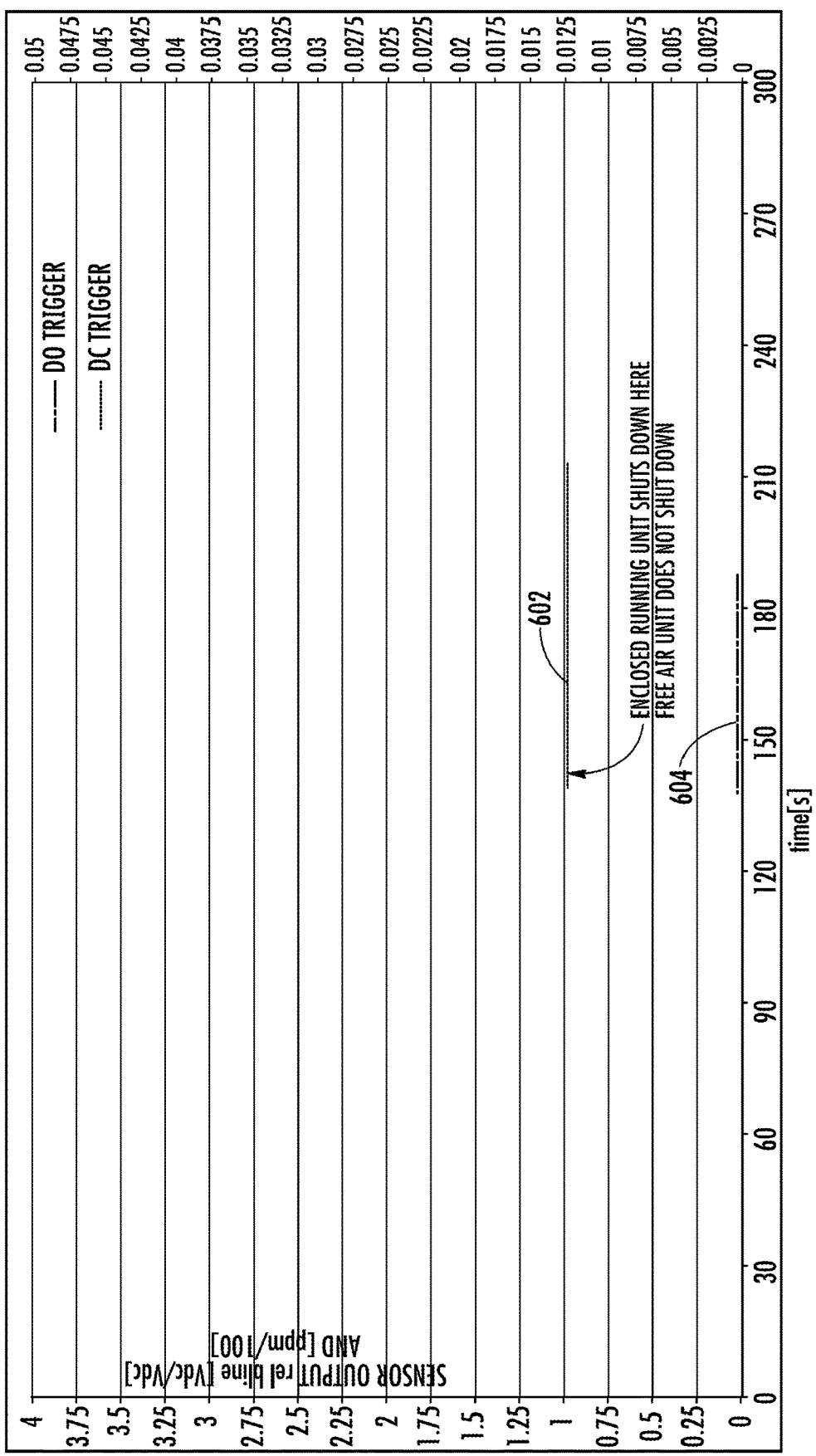
FIG. 14 is a graph of the generator operating time plotted against shutdown thresholds for enclosed and open environment conditions.

Referring to FIG. 14, a graph plotting threshold for shutdown of the generator in both enclosed and open environments against time is shown. As illustrated, the enclosed shutdown threshold 602 is approximately 125 ppm of CO, while the generator in the open environment does not shut down at that threshold (as shown by zeroed-out open environment threshold 604).

Figure 15:
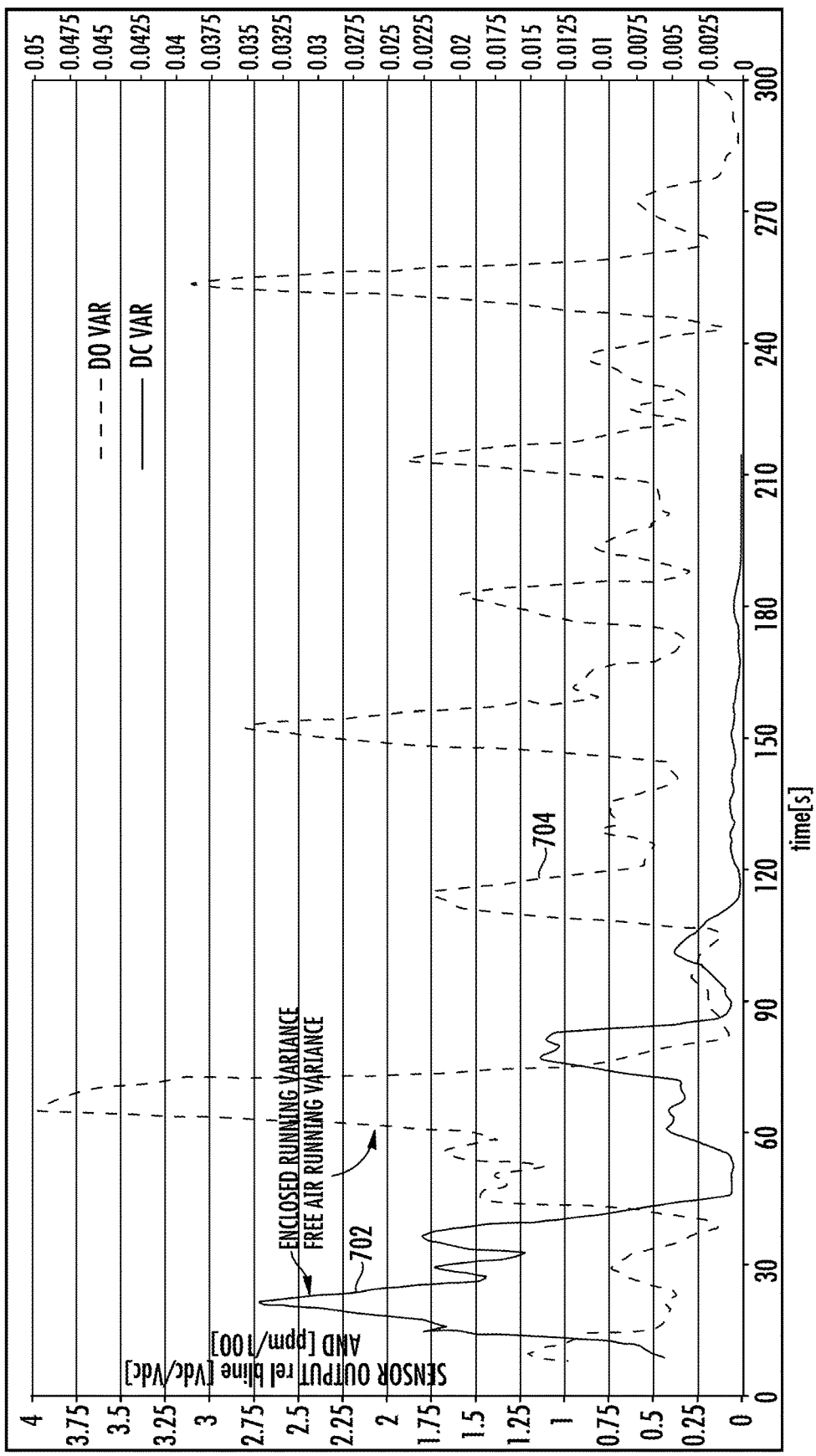
FIG. 15 is a graph of the generator operating time plotted against sensed CO level variances for enclosed and open environment conditions.

Referring to FIG. 15, a graph plotting variance data for both enclosed and open environments against time is shown. To continually monitor the variance, the shutdown circuit 54 described herein compares the current calculated variance to the previously calculated variances for a single generator run. In this regard, the shutdown circuit 54 may temporarily store the readings relating to one or more data samples in a database incorporated with the CO sensor controller 50. To calculate variance, the shutdown circuit 54 uses the above-described variance equation for each sample reading time frame. The variance of the output signal read from the CO sensor 30 is thus calculated using a sample CO reading and the average CO reading over a sample window.

As illustrated in FIG. 15, the enclosed environment variance 702 varies somewhat at the beginning of the test, and then levels out toward a value of zero around approximately 100 seconds. The open environment variance 704 continues to vary over the course of the test. The variance of the sensed values indicates how much the sensed values vary from their average and thus, whether the sensed readings are choppy or smooth when graphed over time signifying that as time increases, the sensed CO values during the enclosed environment test tend to change very little over time (see FIG. 12 showing sensor output value versus time). When sensed readings increase and decrease rapidly over time with a relatively high variance, that may be an indication the generator 10 is in an open environment. When sensed readings change smoothly over time (e.g., steadily increase) with relatively low variance, that may be an indication the generator 10 is in an enclosed environment.

Figure 16:
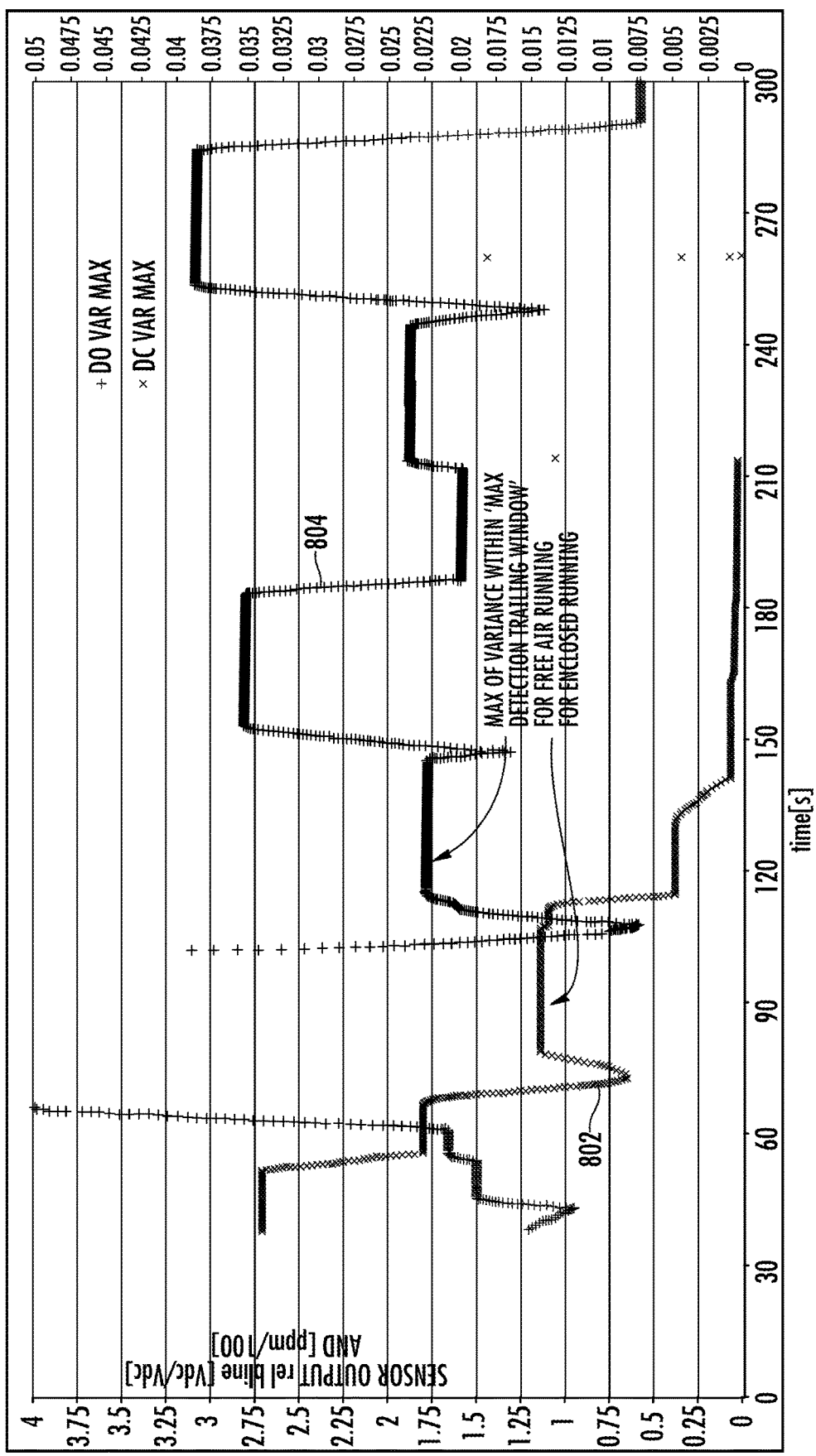
FIG. 16 is a graph of the generator operating time plotted against maximum variance CO levels for enclosed and open environment conditions.

Referring to FIG. 16, a graph plotting maximum variances for both enclosed and open environments against time is shown. As illustrated, the enclosed environment maximum variance 802 decreases over time and the open environment maximum variance 804 continues to vary over time. The shutdown circuit 54 uses the calculated maximum variance over a number of sample readings to determine whether the generator 10 is in an enclosed environment or an open environment. The shutdown circuit 54 continues to calculate variance as described above, while monitoring the maximum value of variance calculated over time. The maximum variance calculated for an enclosed environment (e.g., garage) will be typically lower than the maximum variance calculated for an open environment (e.g., outside). Maximum variance curves vary less than the variance curves described above and thus, may be useful in that the distinction between a graphed maximum variance value for an enclosed environment and an open environment is relatively clear.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively, or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively, or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server).

To that end, a "circuit" as described herein may include components that are distributed across one or more locations.

An exemplary system for implementing the overall system or portions of the embodiments might include a general purpose computing computers in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

What is claimed is:

1. A generator comprising:
   an engine;
   an air-fuel mixing device coupled to the engine, wherein the air-fuel mixing device is structured to receive air from an air intake and combine the air with fuel to create an air/fuel mixture;
   an exhaust outlet structured to emit exhaust gases from the engine; and
   a CO sensor structured to detect CO concentration;
   a CO sensor controller coupled to the CO sensor and structured to control operation of the CO sensor, wherein the CO sensor controller comprises:
   a shutdown circuit structured to:
      determine an environment of the generator, the environment including at least an enclosed environment and an open environment;
      determine a first predetermined threshold for the enclosed environment; and
      determine a second predetermined threshold for the open environment; and
   an alert circuit structured to receive an alert indication from the shutdown circuit and alert a user of the generator to the detected CO concentration.

2. The generator of claim 1, wherein the CO sensor is positioned on an opposite side of the generator from the exhaust outlet.

3. The generator of claim 1, wherein the shutdown circuit is further structured to complete a shutdown procedure upon determining that a maximum CO concentration threshold is exceeded, the maximum CO concentration threshold unrelated to the environment.

4. The generator of claim 1, wherein the shutdown circuit is further structured to complete a shutdown procedure upon determining the generator is in the enclosed environment and the first predetermined threshold is exceeded.

5. The generator of claim 1, wherein the shutdown circuit is further structured to complete a shutdown procedure upon determining the generator is in the open environment and the second predetermined threshold is exceeded.

6. The generator of claim 1, wherein the shutdown circuit determines the environment of the generator by calculating a slope of a variance of output values from the CO sensor.

7. A method of shutting down a generator including an internal combustion engine, the method comprising:
   determining, by a CO sensor controller, an environment of the generator, the environment comprising at least one of an enclosed environment and an open environment;
   determining, by the CO sensor controller, a first predetermined threshold for the enclosed environment and a second predetermined threshold for the open environment; and
   completing, by the CO sensor controller, a shutdown procedure upon determining the generator is in the enclosed environment and the first predetermined threshold is exceeded.

8. The method of claim 7, further comprising:
   receiving, by the CO sensor controller, an alert indication, the alert indication including a determination that the first predetermined threshold and the generator is in the enclosed environment; and
   prior to completing the shutdown procedure, generating, by the CO sensor controller, an alert alerting a user of the generator to the detected CO concentration.

9. The method of claim 7, wherein the shutdown circuit is further structured to complete a shutdown procedure upon determining the generator is in the open environment and the second predetermined threshold is exceeded.

10. A generator comprising:
    an engine;
    an air-fuel mixing device coupled to the engine, wherein the air-fuel mixing device is structured to receive air from an air intake and combine the air with fuel to create an air/fuel mixture;
    an exhaust outlet structured to emit exhaust gases from the engine; and
    a CO sensor structured to detect CO concentration;
    a CO sensor controller coupled to the CO sensor and structured to control operation of the CO sensor, wherein the CO sensor controller comprises:
    a shutdown circuit structured to determine an environment of the generator and complete a shutdown procedure upon determining that a maximum CO concentration threshold is exceeded, the maximum CO concentration threshold unrelated to the environment; and
    an alert circuit structured to receive an alert indication from the shutdown circuit and alert a user of the generator to the detected CO concentration.

11. The generator of claim 10, wherein the CO sensor is positioned on an opposite side of the generator from the exhaust outlet.

12. A generator comprising:
    an engine;
    an air-fuel mixing device coupled to the engine, wherein the air-fuel mixing device is structured to receive air from an air intake and combine the air with fuel to create an air/fuel mixture;
    an exhaust outlet structured to emit exhaust gases from the engine; and
    a CO sensor structured to detect CO concentration;

a CO sensor controller coupled to the CO sensor and structured to control operation of the CO sensor, wherein the CO sensor controller comprises:

a shutdown circuit structured to determine an environment of the generator by calculating a slope of a variance of output values from the CO sensor; and an alert circuit structured to receive an alert indication from the shutdown circuit and alert a user of the generator to the detected CO concentration.

13. The generator of claim 12, wherein the CO sensor is positioned on an opposite side of the generator from the exhaust outlet.

* * * * *